United States Patent
Linares

(10) Patent No.: US 8,454,703 B2
(45) Date of Patent: *Jun. 4, 2013

(54) SHOULDER IMPLANT WITH FIRST AND SECOND COMPOSITE SUB-ASSEMBLIES AND IMPROVED MOUNTING ANCHORS FOR ESTABLISHING A SECURE JOINT

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 190 days.

This patent is subject to a terminal disclaimer.

(21) Appl. No.: 12/465,275

(22) Filed: May 13, 2009

(65) Prior Publication Data

US 2009/0292364 A1 Nov. 26, 2009

Related U.S. Application Data

(60) Provisional application No. 61/054,904, filed on May 21, 2008.

(51) Int. Cl.
A61F 2/40 (2006.01)

(52) U.S. Cl.
USPC .................................................... 623/19.13

(58) Field of Classification Search
USPC ................. 623/19.11–19.14; 411/24, 25, 33, 411/44, 46, 54, 54.1, 79, 80, 80.1, 80.5; 606/64
See application file for complete search history.

(56) References Cited

U.S. PATENT DOCUMENTS

| | | | | |
|---|---|---|---|---|
| 1,051,444 A | * | 1/1913 | Pleister | 411/80.5 |
| 2,314,445 A | * | 3/1943 | Du Vall | 411/44 |
| 2,821,979 A | * | 2/1958 | Cameron | 606/64 |
| 3,694,820 A | | 10/1972 | Scales et al. | |
| 3,815,157 A | | 6/1974 | Skorecki et al. | |
| 4,040,131 A | | 8/1977 | Gristina | |
| 4,045,825 A | | 9/1977 | Stroot | |
| 4,693,723 A | | 9/1987 | Gabard | |
| 4,840,630 A | | 6/1989 | Kitamura | |
| 4,906,149 A | * | 3/1990 | Rockenfeller et al. | 411/54 |
| 5,462,563 A | | 10/1995 | Shearer et al. | |
| 5,507,819 A | | 4/1996 | Wolf | |
| 5,593,448 A | | 1/1997 | Dong | |
| 5,609,647 A | * | 3/1997 | Kalberer et al. | 623/22.24 |

(Continued)

FOREIGN PATENT DOCUMENTS

| | | |
|---|---|---|
| EP | 1228739 A2 | 8/2002 |
| WO | 9800076 A1 | 1/1998 |
| WO | WO-9800076 A1 | 1/1998 |
| WO | WO-2004080331 A2 | 9/2004 |

*Primary Examiner* — Paul Prebilic
*Assistant Examiner* — Marcia Hoffman
(74) *Attorney, Agent, or Firm* — Gifford, Krass, Sprinkle, Anderson & Citkowski, P.C.; Douglas J. McEvoy

(57) ABSTRACT

The present invention discloses an improved shoulder joint implant assembly including a plastic ball secured to a first joint defining bone end face and a plastic receiver secured to a second joint defining bone end face. Each of the ball and receiver implants are constructed of a composite hardened plastic with a softened cartilage wear surface plastic. A fastener is secured to the first joint defining bone end face and over which is mounted the plastic ball. Anchoring of the receiver is established by a pair of integrally formed and inwardly extending mounting tabs, these further extending into further recess machined cavities in the first bone.

5 Claims, 7 Drawing Sheets

U.S. PATENT DOCUMENTS

| | | |
|---|---|---|
| 5,702,469 A * | 12/1997 | Whipple et al. ............ 623/21.15 |
| 5,702,486 A | 12/1997 | Craig et al. |
| 5,723,018 A | 3/1998 | Cyprien et al. |
| 5,741,335 A | 4/1998 | Gerber et al. |
| 5,961,555 A | 10/1999 | Huebner |
| 6,193,758 B1 * | 2/2001 | Huebner .................... 623/19.14 |
| 6,197,063 B1 | 3/2001 | Dews |
| 6,620,197 B2 | 9/2003 | Maroney et al. |
| 6,776,799 B2 | 8/2004 | Ball et al. |
| 6,790,234 B1 | 9/2004 | Frankle |
| 6,986,790 B2 | 1/2006 | Ball et al. |
| 7,033,396 B2 | 4/2006 | Tornier |
| 7,097,663 B1 | 8/2006 | Nicol et al. |
| 7,169,184 B2 * | 1/2007 | Dalla Pria ................... 623/19.12 |
| 7,175,663 B1 * | 2/2007 | Stone ......................... 623/19.13 |
| 7,189,261 B2 | 3/2007 | Dews et al. |
| 7,309,360 B2 | 12/2007 | Tornier et al. |
| 7,445,638 B2 | 11/2008 | Beguin et al. |
| 7,462,197 B2 | 12/2008 | Tornier et al. |
| 7,465,319 B2 | 12/2008 | Tornier |
| 7,510,558 B2 | 3/2009 | Tallarida et al. |
| 2004/0064187 A1 | 4/2004 | Ball et al. |
| 2004/0064188 A1 | 4/2004 | Ball et al. |
| 2004/0210317 A1 * | 10/2004 | Maroney et al. ............ 623/19.14 |
| 2004/0267370 A1 * | 12/2004 | Ondrla ....................... 623/19.11 |
| 2005/0261775 A1 * | 11/2005 | Baum et al. ................ 623/19.12 |
| 2005/0278032 A1 * | 12/2005 | Tornier et al. .............. 623/19.12 |
| 2006/0111787 A1 * | 5/2006 | Bailie et al. ................ 623/19.13 |
| 2007/0005074 A1 | 1/2007 | Chudik |

* cited by examiner

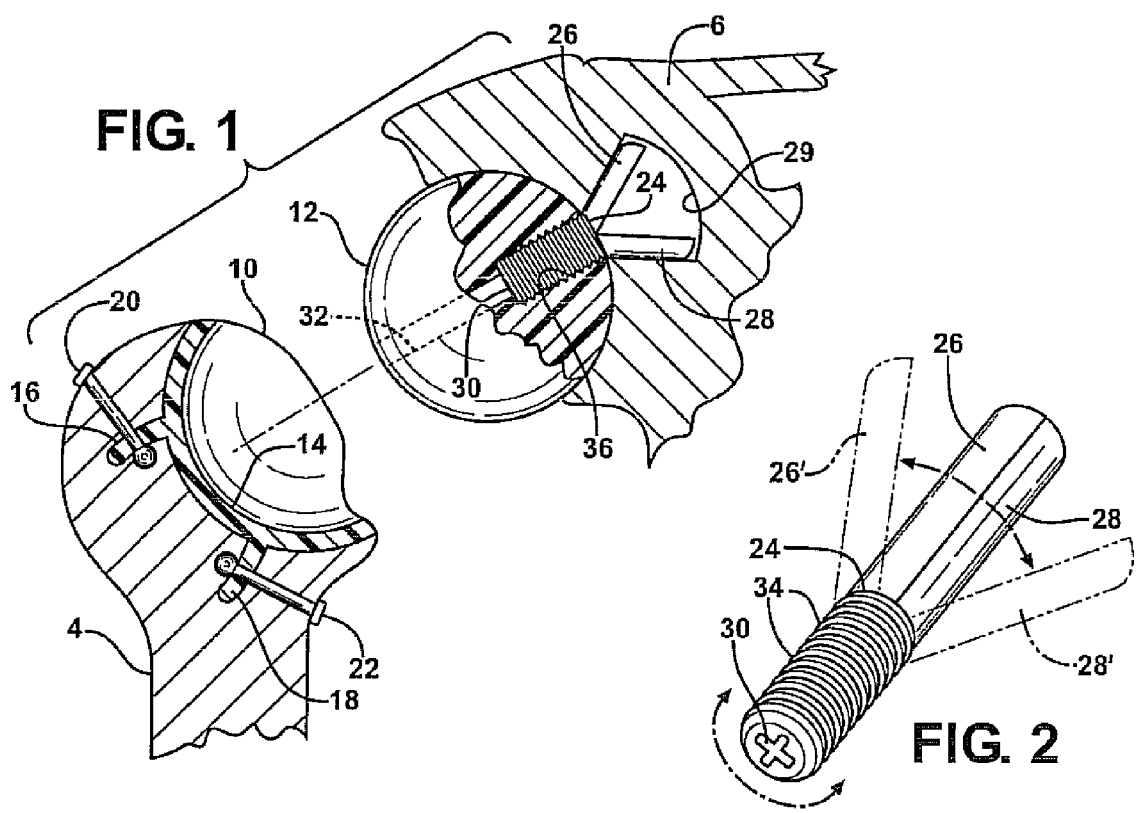
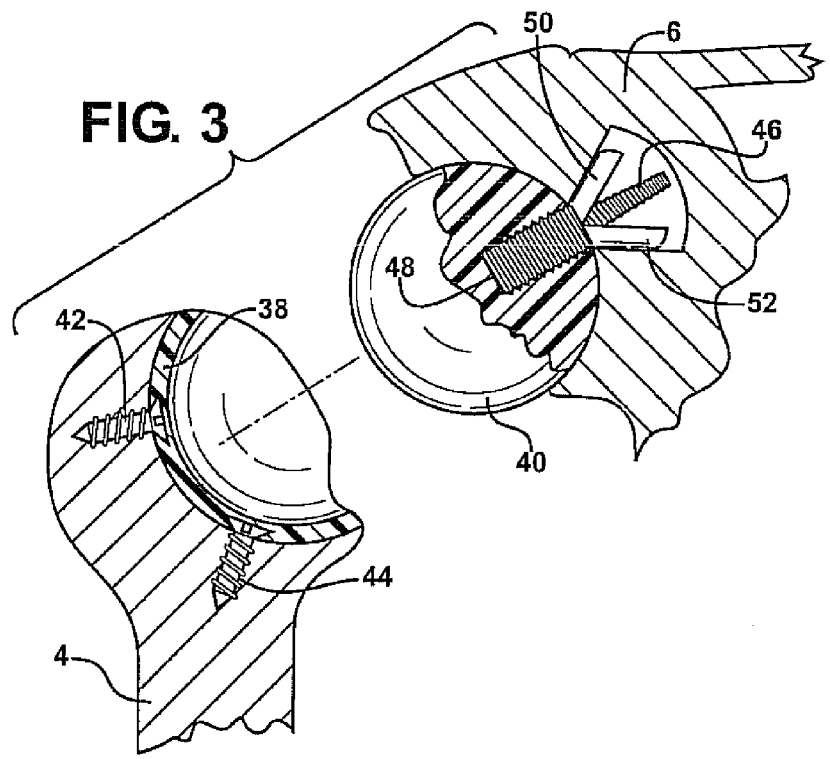

FIG. 10
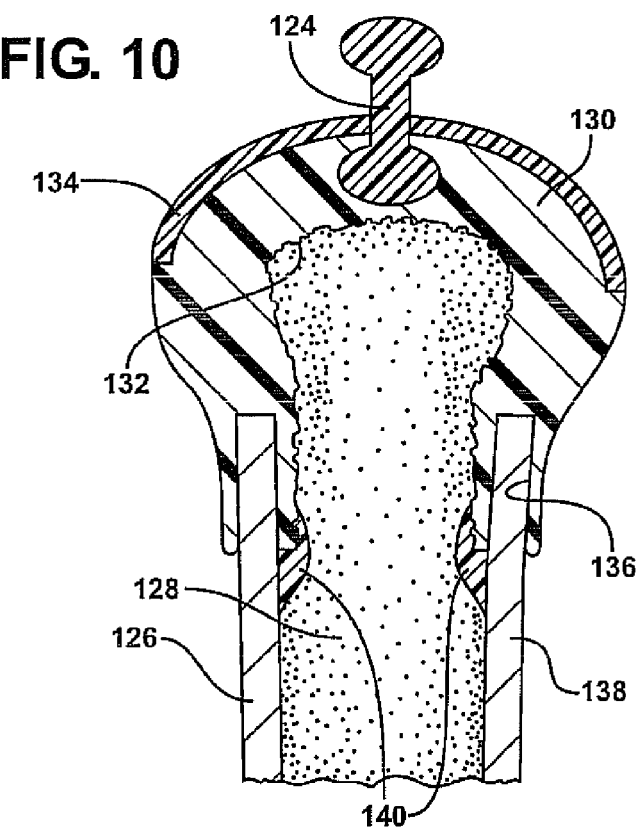
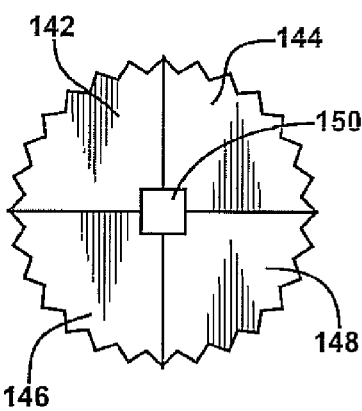
FIG. 11A
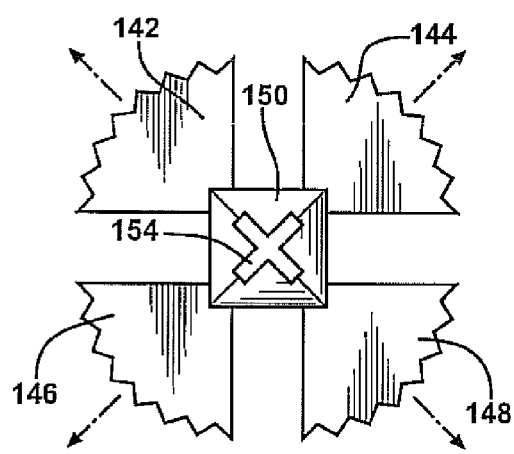
FIG. 11B
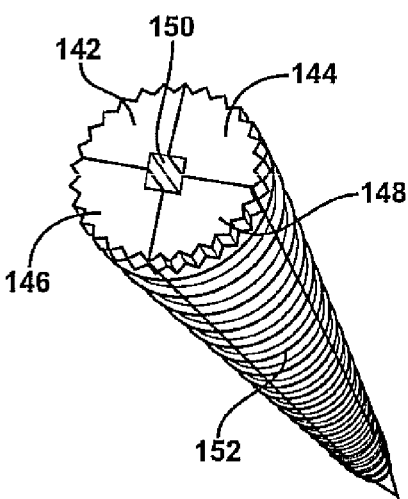
FIG. 11C

SHOULDER IMPLANT WITH FIRST AND SECOND COMPOSITE SUB-ASSEMBLIES AND IMPROVED MOUNTING ANCHORS FOR ESTABLISHING A SECURE JOINT

CROSS-REFERENCE TO RELATED APPLICATIONS

This Application claims the benefit of U.S. Provisional Application 61/054,904 filed on May 21, 2008.

FIELD OF THE INVENTION

The present invention is generally directed to a retrofit shoulder implant assembly. More specifically, the present invention discloses a ball and receiver arrangement for anchor mounting with respect to retrofitted first and second bones associated with a shoulder implant assembly. Each of the ball and socket incorporate a hard plastic substratum, a soft plastic cartilage overlay, and an interior anchoring support drawn from any of a hardened plastic/metal turning screw, a support pin/clip or a bone end machined and receiving rivet.

BACKGROUND OF THE INVENTION

The prior art is well documented with examples of shoulder implant and prosthesis, these typically including a form of ball and socket for securing an upper arm (humerus) bone to a scapula associated with a patient's upper torso. Among numerous examples of shoulder prosthesis devices include such as those disclosed in Stroot U.S. Pat. No. 4,045,825, Scales U.S. Pat. No. 3,694,820 and Gabard U.S. Pat. No. 4,693,723, and in each instance teaches a spherical shaped and humerus extending implant seated within a concave and pocket shaped receiver associated with the scapula/torso area.

SUMMARY OF THE INVENTION

The present invention discloses an improved shoulder joint implant assembly with enhanced anchoring capabilities for securely positioning the joint defining structure and including a plastic ball secured to a first joint defining bone end face and a plastic receiver secured to a second joint defining bone end face. Each of the ball and receiver implants are constructed of a composite hardened plastic with a softened cartilage wear surface plastic. A fastener is secured to the first joint defining bone end face and over which is mounted the plastic ball. Anchoring of the receiver is established by a pair of integrally formed and inwardly extending mounting tabs, these further extending into further recess machined cavities in the first bone.

Additional features include the provision of support pins for anchoring the mounting tabs into location with the first bone. At least one of the ball and receiver defined locations further can include a single layer of a composite soft plastic material having rearward extending and integrally formed portions configured, so as to precisely match machined interior locations associated with the associated bone and in preparation for installation thereto.

The ball may also include an undercut support mounted to a scapula bone. A rotating flexible ligament extends from the support and a first composite hard plastic material is applied over the scapula and seats within a second composite hard plastic associated with the receiver and defining an end-mounting location of a humerus bone. The second hard plastic further secures, via an undercut profile, with a machined end of the humerus bone. A soft plastic layer is overlaid onto each of said hard plastic materials and arranged in an opposing and joint defining fashion to provide for substantially frictionless and long-term wear.

Yet additional variants include the provision of an axially displaceable anchor including a plurality of portions supported via an elongated and central supporting key actuating stem the anchor portions displaceable to a second expanded position once positioned within a recess defined area sectioned into the adjoining bone. Another variant teaches a deformable plastic collar enclosing a pair of laterally displaceable and semi-spherical shaped undercut portions, these responding to downward actuation of a spike portion positioned in communication with a central passageway in the sleeve and resulting in the displacement of the undercut portions outwardly deforming the side walls of the encapsulating sleeve, such as to seat within a previously machined undercut within the bone of the patient.

A further modified version of anchoring screw also incorporates a downwardly displaceable spike and exhibits a reconfigured sleeve with first and second end extending and laterally displaceable portions defined in communication with an interior and lengthwise extending passageway associated with the sleeve. A further configuration of anchoring sleeve exhibits first and second linearly separated and laterally displaceable halves which are actuated via an inwardly engaging spike and in which the separated sleeve halves are supported in their laterally displaced condition by a combination of the inwardly displacing and engaging spike and the annular side walls associated with the bone drill hole.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is an exploded view of a receiver and ball arrangement configured between such as a humerus and scapula bones and including retrofit mounted first and second components which, when installed, provide a durable and long-term wear resistance in use;

FIG. 2 is a sectional illustration of a mounting screw employed with the ball mounting arrangement in FIG. 1 and with laterally and pivotal separable tail portions, such as for securely anchoring in place with respect to a mounted bone end face location;

FIG. 3 is a similar exploded view of a further related variation of shoulder implant and in particular utilizing a variation of a hardened plastic screw associated with the end mounted socket;

FIG. 10 is an illustration of an alternate arrangement to that shown in FIGS. 15 and 16, and by which a differently configured hardened plastic end plug is secured to a sectioned end of a natural bone, within which is contained bone marrow, the end plug further exhibiting a recessed interior facing surface which is ribbed or otherwise irregularly formed so that marrow contact locations promote the growth of adhering healthy bone;

FIG. 11A is a top end illustration of an axially displaceable anchor including a plurality of portions supported via an elongated and central supporting key actuating portion;

FIG. 11B is a succeeding illustration to FIG. 11A and showing the supported anchor portions displaced to a second expanded position;

FIG. 11C is a perspective view of the anchor in the expanded position of FIG. 11B;

DETAILED DESCRIPTION OF THE PREFERRED EMBODIMENTS

Figure 4:
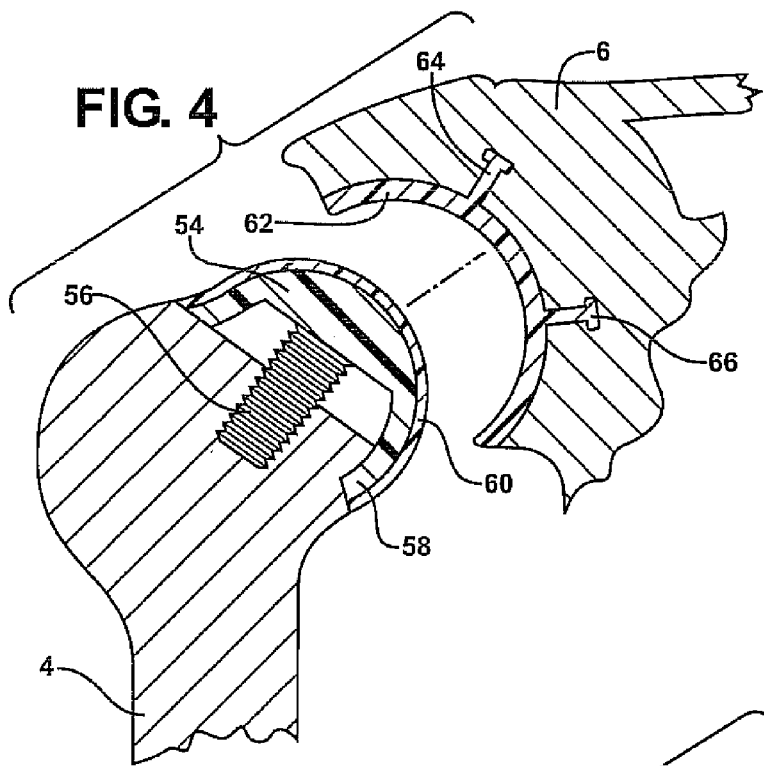
FIG. 4 is an exploded view of a further alternate variation of shoulder implant assembly and by which a modified end mounting arrangement is employed for retrofit securing a modified ball to an end face of an upper humerus bone.

As previously described, the present invention discloses an improved anchoring system for use in mounting a ball and receiver arrangement with respect to retrofitted first and second bones associated with a shoulder implant assembly. As will be described in each of the succeeding illustrations, each of the ball and socket mounted implants incorporate one or more of a hard plastic (or composite plastic) substratum, a soft plastic cartilage overlay, and an interior anchoring support drawn from any of a hardened plastic/metal turning screw, a support pin/clip, an expandable anchor for securing to a machined undercut, or a bone end machined and receiving rivet.

Prior to discussing the various embodiments set forth collectively in FIGS. 1-5, FIG. 6 is a prior art description of typical human skeletal structure 2. A shoulder joint configuration is generally referenced by an upper humerus bone 4, this seating within a generally receiver end location associated with a scapula bone 6. The scapula 6 is in turn integrated into the individuals' torso and further connects, such as by clavicle 8, to the remainder of the upper body skeletal structure, e.g. including rib cage, spine, etc. While illustrating a preferred application in use with a human shoulder joint, it is also envisioned and understood that the shoulder implant assembly according to the present invention can also be utilized with other mammal species.

Having provided a brief overview of the skeletal specifics, reference will now be made to the illustrations set forth in FIGS. 1-5. Also, and as will be described with reference to the various succeeding illustrations, the shoulder implant configurations incorporate novel installation procedures which serve to minimize associated damage, such as to ligaments, tendons and the like and in order to reduce patient recovery/rehabilitation time.

While not shown, it is understood that either natural or synthetic ligaments and the like can be utilized in the joint assemblies described herein. Furthermore, and while also not illustrated, appropriate medical drill technology is also contemplated and which can be employed both in the reconditioning of a patients humerus and/or scapula, such as in order to prepare existing bone surfaces for receiving a prosthetic shoulder implant such as according to the numerous embodiments disclosed herein. Such drill technology can include the provision of appropriately configured bits for producing a first drill hole in a reconditioning surface of a bone, following which a second undercut hole of greater diameter or configuration is formed at a recessed location within the primary hole, this in order to seat, engage and permanently secure an associated anchor portion and which in turn maintains a desired arrangement and positioning of the ball and receiver elements which are fixed to the anchor portions.

Referring now to FIG. 1, an exploded view is shown of a first receiver 10 and seating ball 12 arrangement configured between such as the humerus 4 and scapula 6 bones, respectively, this including retrofit mounted first and second components which, when installed, provide a durable and long-term wear resistance in use. In this embodiment, the receiver 10 further consists of a composite hardened plastic material in a generally inwardly bowl configuration, which is further of a desired thickness and is mounted to a properly (inwardly concave or recess) prepared and retrofitted end face associated with an upper facing surface of the humerus 4. The ball 12 is further constructed of a composite plastic or like material, and can include a mixture of hard and soft plasticized components for increasing wear life.

As will also be described in reference to the several succeeding embodiments, an over-layering of a softened and cartilage supporting plastic material which exhibits substantially frictionless properties can also be applied to (other otherwise intermixed with) the composite material. It is further understood that the plastic and composite plastic materials may further include the use of such as anti-microbial or sanitary plastics, this helping to prevent infection.

As is shown in FIG. 1, the end face of the humerus bone 4 is suitably machined/prepared, such as utilizing state of the art equipment for hollowing out the facing end of the bone in a like mating fashion and for preparing for installation of the joint implant assembly in situ (or inside the body cavity). The inwardly bowled receiver cup 10, as shown in cutaway, is further configured so as to include a concave surface over which his layered a cartilage composite plastic layer 14, this for receiving and seating in pivoting fashion a mating ball 12.

Anchoring of the receiver is further accomplished by the provision of a pair of integrally formed and inwardly extending mounting tabs 16 and 18, these extending from reverse facing surfaces of the concave shaped receiver layer 14, and extending into aligning recess machined cavities associated with the interior of the humerus bone 4 in proximity to the receiver 10 mounting. Support pins 20 and 22 are also shown for anchoring the mounting tabs 16 and 18 into the indicated locations within the humerus bone, the pins being seated within the previously drilled holes with or without undercut formed holes as previously described.

As is also shown in FIG. 2, an embedded and ball supporting fastener (also mounting screw) 24 is illustrated with laterally and pivotal separable wing or tail portions, see as folded at 26 & 28, as well as laterally and oppositely displaceable at 26' and 28, this such as for securely anchoring in place with respect to the mounted (scapula) bone 6 in the configured end face location in FIG. 1. In application, the scapula bone mounting location is first prepared, such as by machining or otherwise drilling/shaping a generally corresponding and dovetail like mounting configuration (see at 29 again cutaway of FIG. 1) within the bone. This further contemplates the formation of increased interior dimensions within the bone, this communicating with a surface mounting location via such as a narrowed neck portion (the mounting location of the screw 24 in FIG. 1 renders readily apparent the mating and interior machining profile which must be associated with the installation of the screw 24).

A surface projecting portion of the fastener 24 is further exhibited by a screwdriver head portion 30, this being design so as to be rotatable relative to the expandable wing/tail portions 26 and 28, and thereby to securely anchor the fastener 24 within the bone 6. Along these lines, it is envisioned that any suitable mechanical linkage or structure can be employed for facilitating the wings 26 and 28 to laterally displace, and as a result of rotation, such as by a screwdriver (not shown), of the accessible head portion 30.

As further shown in FIG. 1, the head portion 30 of the expandable fastener 24 can either be pre-mounted to the ball 12, such that a shaft of the screwdriver is accessed through an aperture defined in the ball 12 (see inner extending surface associated with screwdriver access hole at 32 in FIG. 1). Alternatively, the fastener 24 can be pre-engaged within the dovetailed/undercut defined aperture 29, via the lateral expansion of the wing portions 26 and 28 (again FIG. 1), following which the ball 12 is installed by rotating and threadably engaging exterior threads 34 associated with the screw portion 24 with additional interior threads (see at 36) configured upon an inner facing wall associated with a recess formed in the ball 12 for permitting the ball to be mounted to the fastener 24.

Referencing further FIG. 3, a similar exploded view is shown of a further related variation of shoulder implant, this again including a first receiver implant 38 and mating ball implant 40. The arrangement of FIG. 3 is functionally similar that of FIG. 1, and by which a retrofit installed implant assembly is provided for a shoulder joint application. Although again not shown, it is understood that a suitable arrangement of cartilage and ligaments are provided for establishing a secure and properly aligning joint profile.

Variations of the configuration shown in FIG. 3 include the receiver 38 which, while again exhibiting a concave cup shaped seating profile and an option surface layering of a soft cartilage defining plastic, may also be anchored in an alternate fashion, and by the use of a pair of spikes or screws 42 and 44. With further reference to the ball 40, a similar mounting arrangement is employed for securing to a projecting end of a modified and embedded fastener, this further illustrating an embedded spike portion 46 and which can be constructed of a hardened plastic or like material.

A rotatable and enlarged diameter screw head 48 associated with the fastener 42 is similarly actuated to laterally displace a modified arrangement of wing-like portions 50 and 52, these evidencing another arrangement for securely anchoring the fastener 46 and, by extension, the composite ball 40. As with the implant ball 12 illustrated in FIG. 1, the ball 40 in FIG. 3 can incorporate an interiorly threaded recess for mounting to the projecting screw head portions of either fastener design. Alternatively, the ball configurations can be securely mounted through other techniques, and in order to prevent inadvertent separation of the ball from the fastener in use.

Referring now to FIG. 4, an exploded and cutaway view is shown of a further alternate variation of shoulder implant assembly, and by which a modified end mounting arrangement is employed for retrofit securing a modified and pseudo-convex shaped ball 54 to a machined end face of the upper humerus bone 4. The implant ball 54 as shown is generally a reversal of the concave cup-shaped seating profiles associated with the humerus in FIGS. 1 and 3 and further illustrates the reversibility of the present design.

The composite and hardened plastic construction of the implant mounting ball 54 finder exhibits any number of integrally formed and inwardly projecting/seating portions, see as shown by generally centrally located screw support at 56 as well as lower configured end surface 58, and to which the end surface of the bone 4 is matingly machined in order to neatly secure and seat the implant 54. An overlaying of soft composite plastic 60 is also provided for implant ball 54. The upper humerus design of FIG. 4 contemplates a substantial retrofit/repair to the bone joint location, this arising from a number of circumstances including traumatic injury, bone degenerative disease, or the like.

The upper (scapula) bone 6 in FIG. 4 further contemplates an arrangement by which use of a hardened plastic substrate is excluded in favor of a single layer of a composite soft plastic material 62. Mounting of the implant material layer 62 is facilitated by rearward extending and integrally formed portions 64 and 66, these including stem portions from which extend end undercut portions which in turn are configured so as to precisely match machined interior locations associated with the scapula bone 6 and in preparation for installing the end surface defining implant.

Figure 5:
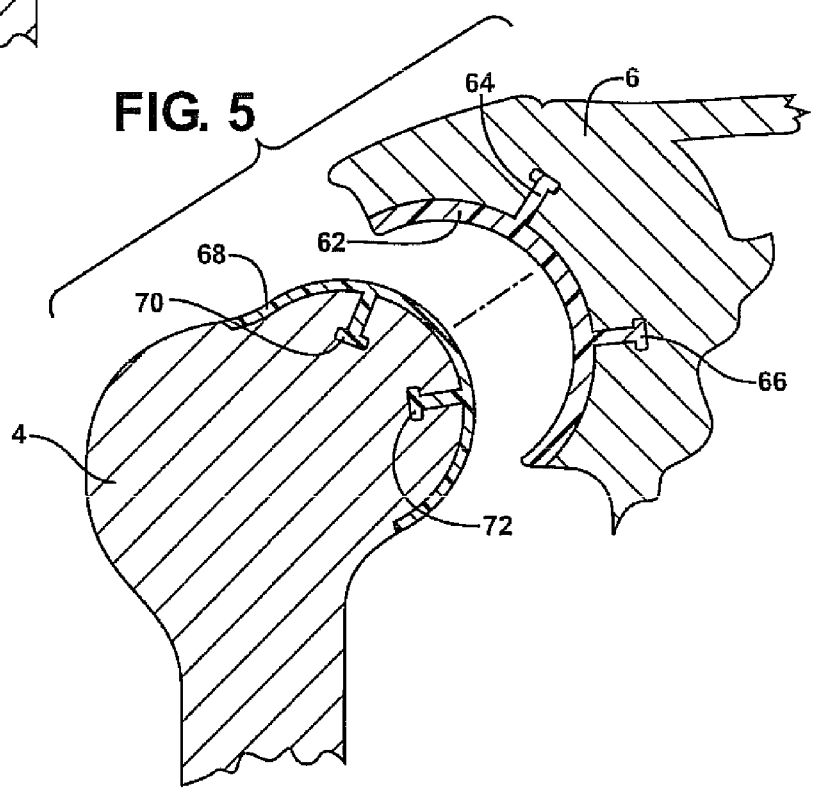
FIG. 5 is a related illustration to that in FIG. 4, and by which first and second soft plastic (cartilage) portions are exclusively substituted along ball and receiver locations associated with the humerus and scapula mounting location.
Figure 6:
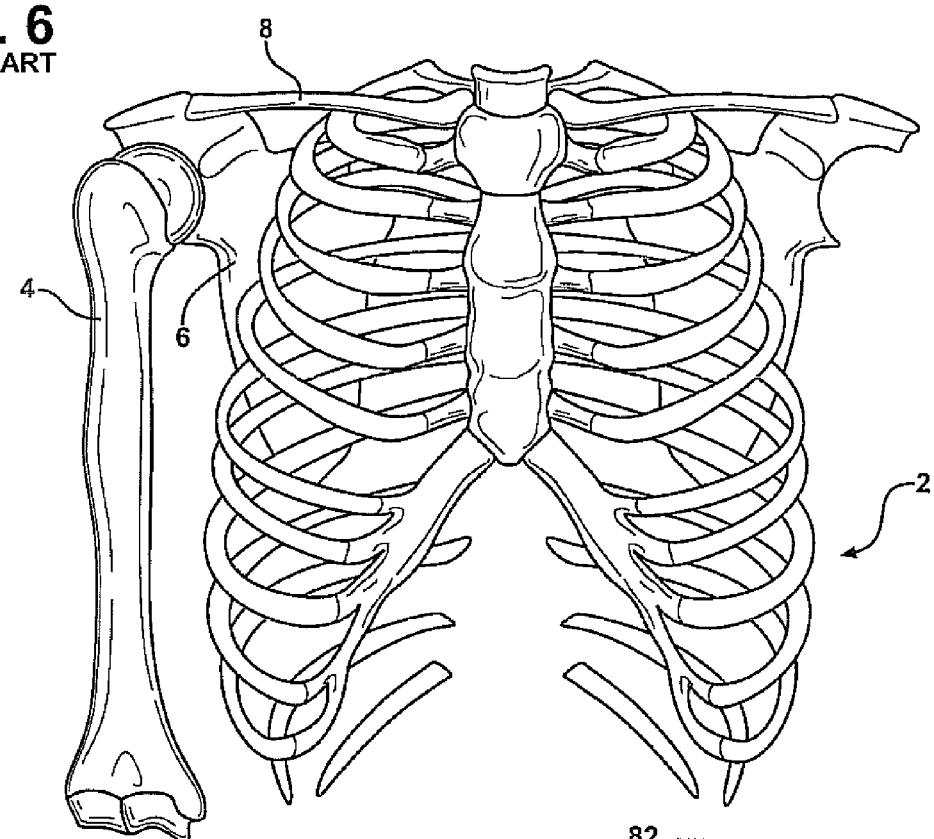
FIG. 6 is a prior art description of typical human skeletal structure illustrating a typical arrangement of an upper humerus with a scapula.

Referring to FIG. 5, a related illustration to that in FIG. 4 illustrates both first and second soft plastic (cartilage) portions being exclusively substituted for both the ball and receiver locations associated with the humerus and scapula mounting locations. The scapula 6 mounting arrangement in FIG. 6 is identical to that shown in FIG. 5, with the humerus bone 4 exhibiting a like single layer of a composite soft plastic material 68, this again further including the provision of rearward extending and integrally formed stem and end supported undercut portions 70 and 72 configured to precisely match machined interior locations associated with the humerus bone 4, and again in preparation for installing the end surface defining implant. The arrangement of FIG. 5 contemplates use where the pre-existing damage to the humerus and scapula are of a generally minor nature, such that sufficient reconditioning can be accomplished without removal of substantial bone mass and such as further which is characterized by a number of the preceding variants which require the mounting of the spherical shaped prosthetic ball.

Figure 7:
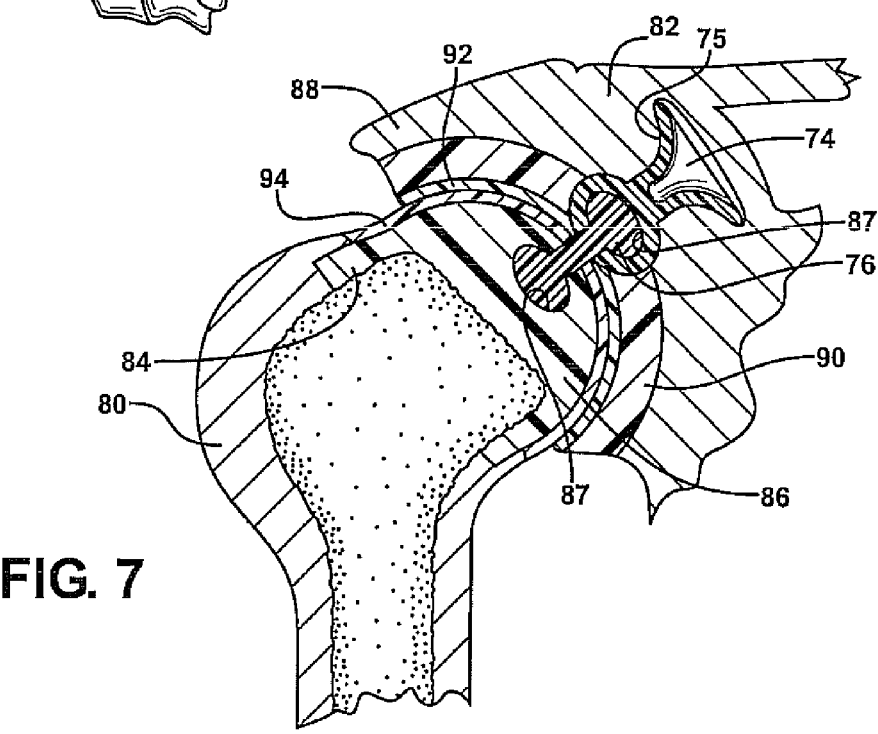
FIG. 7 is a further alternate illustration of a shoulder implant and exhibiting a rotating under cut support and associated flexible ligament for supporting an end-modified humerus relative to a scapula.

Referring now to FIG. 7, a further alternate illustration of a shoulder implant is shown in cutaway and exhibiting a rotating under cut support 74 and associated flexible ligament 76 for supporting an end-modified humerus 80 relative to a scapula 82. Similar to what is again shown at 29 in FIG. 1, a dovetail shaped undercut is defined n a recessed location within the scapula 82 and in order to seat in secure position a generally bell shaped portion of the durable plastic undercut support (see at 75). The humerus 80 includes a sectioned and notched bone end (see stepped end profile 84) within which is engaged (such as by adhesive and/or natural marrow adhesion) a composite and three dimensional shaped hard plastic insert 86.

As shown, a first annular enlarged end of the ligament 76 (and which establishes a modified dumb-bell or spool shape in outline) is embedded within a mating recess with undercut profile (see at 87) formed in the composite hard plastic insert 86, whereas a second, optionally enlarged, annular end seats within a lower defined and annular shaped opening 87 associated with the three dimensional shaped and mounted undercut support 74 in turn supported in seating fashion within a sectioned aperture defined in an upper bone 88 associated with the scapula. An upper composite hard plastic material exhibiting a generally inward concave/bowl shape is shown 90 in overlaying fashion over the bone 88 and support 74, with additional and opposing layers of composite soft plastic (or metal) layers 92 and 94 being applied over the composite plastics 86 and 90, respectively. In use, the undercut support 74 and rotating flexible ligament 76 provide the combined features of resiliency, long wear resistance, and universal (swivelable) rotation between the humerus and scapula bones.

Figure 8:
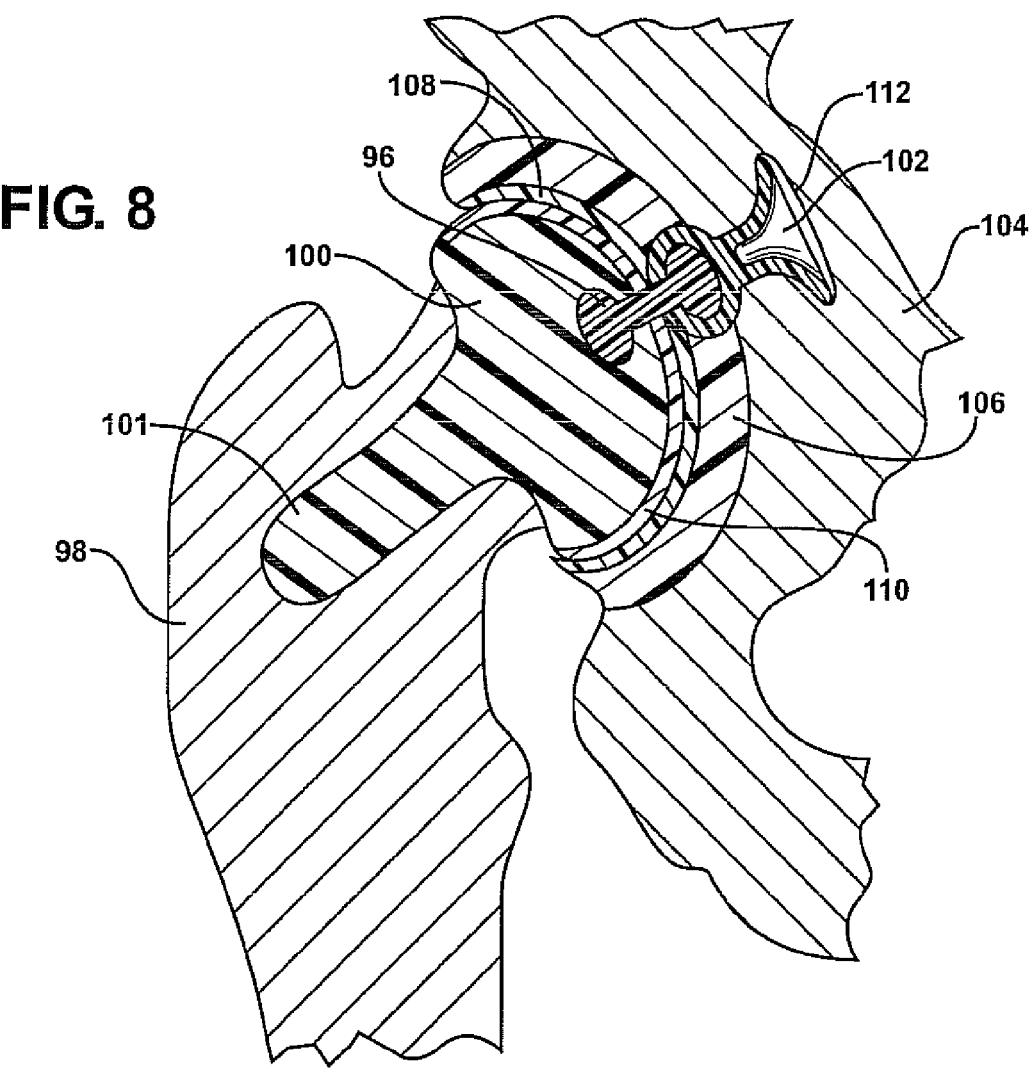
FIG. 8 is an illustration of a further variant of swivelable joint assembly and in which a rotating flexible ligament of substantial spool shape is arranged in a socket configuration between a lower male end defining bone and an undercut support secured to an upper socket defining bone.

Referring now to FIG. 8, an illustration is shown of a further variant of swivelable joint assembly and in which a rotating flexible ligament of substantial spool shape 96 is arranged in a socket configuration between a lower male (or receiver) end defining bone 98, this including a composite hard plastic end plug 100 which is mounted via an integrally configured stem 101 to the bone 98, and an undercut configured and anchoring support 102 secured to an upper socket defining bone 104 and further including a likewise hard plastic arranged in a generally bowl-receiving shape 106. The arrangement shown in FIG. 8 can depict such as a hip or shoulder joint, and in which a desired degree of combined universal and rotatable support is established by the artificially constructed joint. As shown in previously described embodiments, opposing surface locations associated with the composite hard plastic bones 100 and 106 further include composite soft plastic surfaces 108 and 110, the first hardened plastic plug 100 further including an extending stem portion which is securably mounted within an interior associated with the bone 98, whereas the second bowl shaped hardened plastic shape 106 is secured via adhesives or a naturally ribbed or irregularly shaped surface for promoting natural bone marrow incorporation and adhesion to the upper bone defined socket 104.

The anchoring support 102 is further provided in a generally knob-shape or like configuration which is similar in numerous respects to that previously described at 74 in FIG. 7 and which can also be constructed of a suitable durable plastic or like composite material. The anchoring support 102 is secured within an aperture 112 formed through the upper saucer shaped bone 104 and associated hardened plastic 106. The rotating flexible (e.g. spool shaped) ligament 96 is swivelable both in respect to the upper located undercut support 102, as well as the recessed (e.g. press fit) mounting location associated with the lower male defining plug 100. In a preferred application, the knob shaped undercut support can also rotate independently or in unison with the spool shaped ligament 96.

Figure 9:
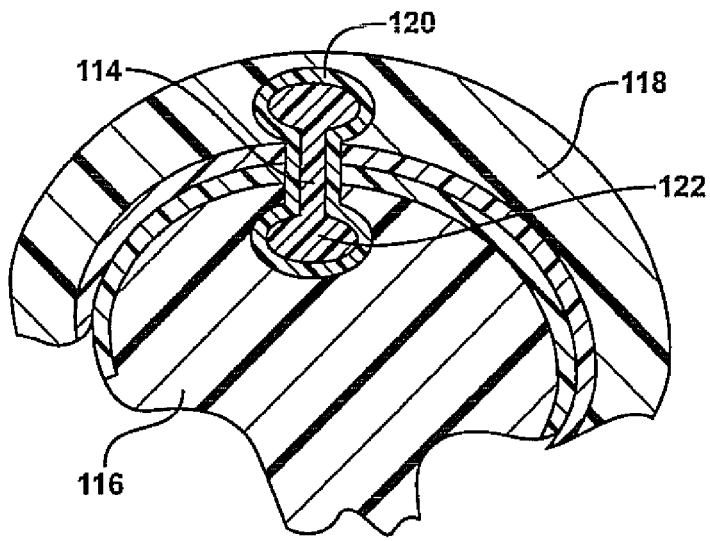
FIG. 9 is an enlarged sectional view of a modified spool shaped rotating and flexible ligament disposed between swiveleable contact locations associated with receiver/socket composite hardened plastic end plugs.

Progressing to FIG. 9, an enlarged sectional view is shown of a further variant of spool shaped rotating and flexible ligament, at 114, disposed between swivelable contact locations associated with a modified and composite hardened plastic lower installed end plug 116 and an upper hardened plastic end plug 118. The spool shaped ligament 114 differs from that previously identified at 96 in that a first exterior layer 120 is applied over a second core material 122. In one preferred application, the exterior layer 120 is a softer/cushioning material, as compared to a hardened core 122. It is also understood that the material compositions can be reversed with the core incorporating a softer material and in comparison to a hardened outer layer, this providing variances in the performance characteristics of the universal joint in use.

Referring to FIG. 10, an illustration is shown of an alternate arrangement to that shown in FIG. 15 or 16, and by which a differently configured hardened plastic plug, likewise generally spool shaped as shown at 124, is secured to a sectioned end of a natural bone 126, within which is contained bone marrow 128. An associated and three dimensional shaped implant 130 exhibits a recessed interior facing surface 132 which is ribbed or otherwise irregularly formed, and such that marrow contact locations promote the growth of adhering healthy bone.

Similar to the several previous embodiments discussed, the end plug 124 is further illustrated in a recess cavity secured (or press fit) fashion within an exposed end face location of the hardened plastic implant 130, and further showing a plastic cartilage defined surface 134 associated with the exposed face of the implant 130. As is further shown in FIG. 10, an annular end face of the implant 130 can exhibit an interior notched recess 136, this being configured and dimensioned to seatingly engage over the exposed and sectioned end (see at 138) of the retrofit/reconditioned bone 126, at which point the interiorly contained marrow 129 initiates its natural bonding action (see as further shown at 140) and which naturally occurs at a boundary location established between the hardened plastic implant 130 and the bone 126.

Referring now to FIGS. 11A-11C, a succession first closed and second open end views are shown of a laterally displaceable anchoring screw. Specifically, and as is further shown by the perspective view of FIG. 18C, the anchoring screw includes a plurality of individual and linearly extending portions, see in the illustrated example as shown by four individual portions 142, 144, 146 and 148 associated with the anchoring screw and which are outwardly displaced relative to a central supporting actuating portion 150

In one preferred variant, the linearly expandable portions 142-148 are limited to top end situated disk portions or the like, these being slidably supported upon a one piece and integrally formed body 152 (again FIG. 11C) and which are displaced between the positions illustrated in FIGS. 11A and 11B via rotation of other engagement action associated with the central supporting stem 150. The actuating portion 150 can exhibit a Philips screwdriver aperture, see at 154, or other suitable engagement location for rotating the portion 150 and in turn outwardly displacing the slidably supported and expandable portions 142-148.

Although not shown, it is also understood and envisioned that the central actuating portion 150 can be reconfigured as a cam surfaced or other suitable portion, and Which upon being key accessed or otherwise actuated/rotated can co-act upon inwardly facing and mating surfaces associated with the expandable portions and in order to displace the same in the manner shown. Additional variants further contemplate the screw body 152 exhibiting a different or narrowed profile depending upon the bone securing location being contemplated. Other pluralities of laterally displaceable portions, including such as two, three or other, are also envisioned. The turn key aperture 154 can be designed so that it may be accessed by a surgeons key and in order to outwardly and laterally displace the individual portions 142-148 in the fashion shown and once the anchor screw has been pre-installed within a specified and pre-machined bone location.

Figure 12A:
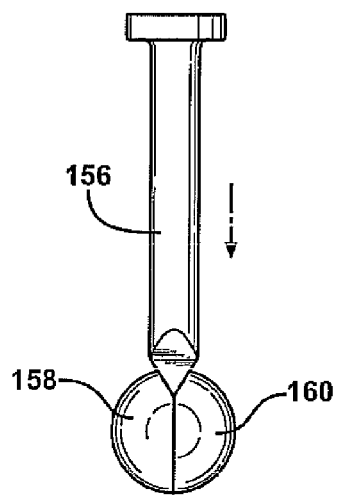
FIG. 12A is an illustration of a spike portion and associated first and second undercut engaging portions associated with a further variant of laterally displaceable anchor and in a pre-laterally displaced condition.

FIG. 12A is an illustration of a spike portion 156 and associated first 158 and second 160 undercut engaging portions, these associated with a further variant of laterally displaceable anchor and in a pre-laterally displaced condition. Succeeding illustration FIG. 12B, further shows the spike 156 in a downwardly displaced and engaged position resulting in lateral expansion of the undercut portions 158 and 160 and by virtue of the pointed end of the spike 160 engaging opposing and inwardly tapered profile edges 162 and 164 associated with upper surfaces of the undercut portions 158 and 160, respectively.

Figure 12B:
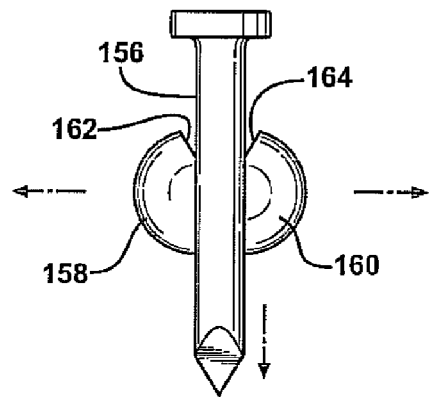
FIG. 12B is a succeeding illustration to that shown in FIG. 12A in a further showing the spike in a downwardly engaged position resulting in lateral expansion of the undercut portions.
Figure 13A:
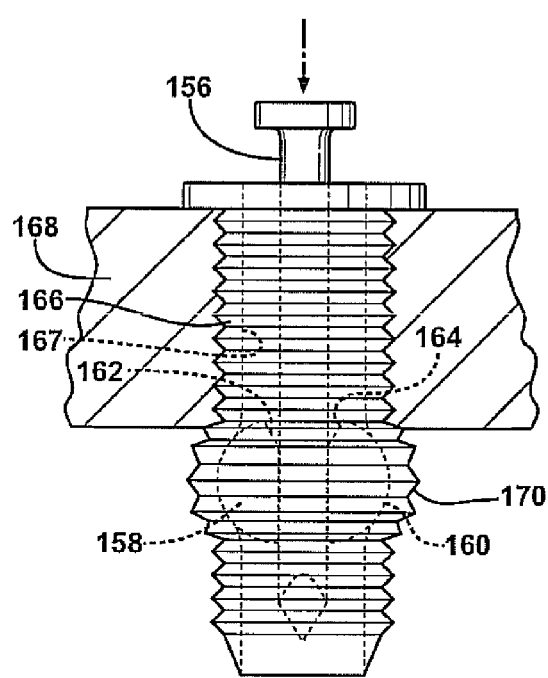
FIG. 13A is an illustration showing the spike and undercut portions of FIGS. 12A-12B incorporated into an elongated and deformable plastic collar and further illustrating the manner in which the laterally displaceable and semi-spherical shaped undercut portions respond from the downward actuation of the spike portion to outwardly deform the side wall of the encapsulating sleeve.

As further shown in FIG. 13A, the spike 156 and undercut portions of FIGS. 12A-12B are now shown incorporated into an elongated and deformable plastic collar (also termed a sleeve anchor) 166, the collar 166 in turn exhibiting exterior threads and which is embedded or otherwise engaged with a bone 168. The cutaway of FIG. 13A further illustrates the manner in which the laterally displaceable and, typically, semi-spherical shaped undercut portions 158 and 160 respond from the downward actuation of the spike portion 156, such as which travels through a communicating interior recess (see inner side wall in phantom at 157) defined within the collar 166, and in order to outwardly deform the indicated side wall position 170 of the encapsulating sleeve 166, this further such as to engage the expandable undercut portions within a machined undercut recess (not shown) in the bone and for providing secure and permanent anchoring of the associated implant (such as ball shaped humerus mounted implant as illustrated in preceding embodiments).

Figure 13B:
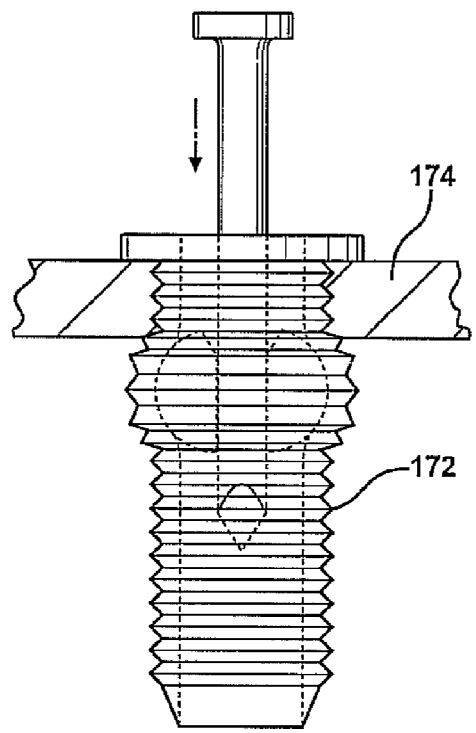
FIG. 13B is an illustration similar to FIG. 13A and of an alternately configured plastic collar utilized in a modified anchor mounting configuration for fastening to a bone wall of reduced thickness.

FIG. 13B is an illustration similar to that shown in FIG. 13A of an alternately configured plastic collar, see as shown at 172, and utilized in a modified anchor mounting configuration for fastening to a bone wall 174 of reduced thickness. Otherwise, the arrangement interior passageway proximate and tapered undercut portions operates in the same fashion as described in FIG. 13A.

Figure 14:
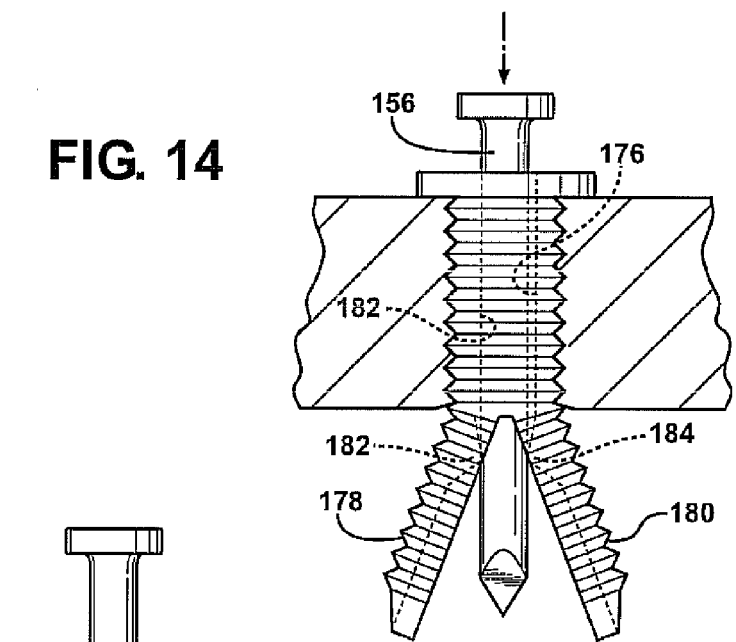
FIG. 14 is an illustration of a modified version of anchoring screw for use with a downwardly displaceable spike and which exhibits a reconfigured sleeve with first and second end extending and laterally displaceable portions defined in communication with an interior and lengthwise extending passageway associated with the sleeve.

Referring now to FIG. 14, an illustration is shown of a modified version of anchoring screw for use with a downwardly displaceable spike and which exhibits a reconfigured sleeve 176 with first 178 and second 180 end extending and laterally displaceable portions defined in communication with an interior and lengthwise extending passageway 182 associated with the sleeve. As further shown, FIG. 14 illustrates one possible configuration of linkage for causing outwardly lateral deflection of the end extending sleeve portions 178 and 180 in response to inward engagement of the associated spike, again at 156. As illustrated, the lower passageway includes an inwardly defined and opposing tapered profile, see at 182 and 184, this creating a structural weakened connection at a location associated with the lower most extending (undercut seating) sleeve portions 178 and 180 and allowing the same to pivot outwardly in the manner shown upon the downward/inward engagement of the spike.

Figure 15A:
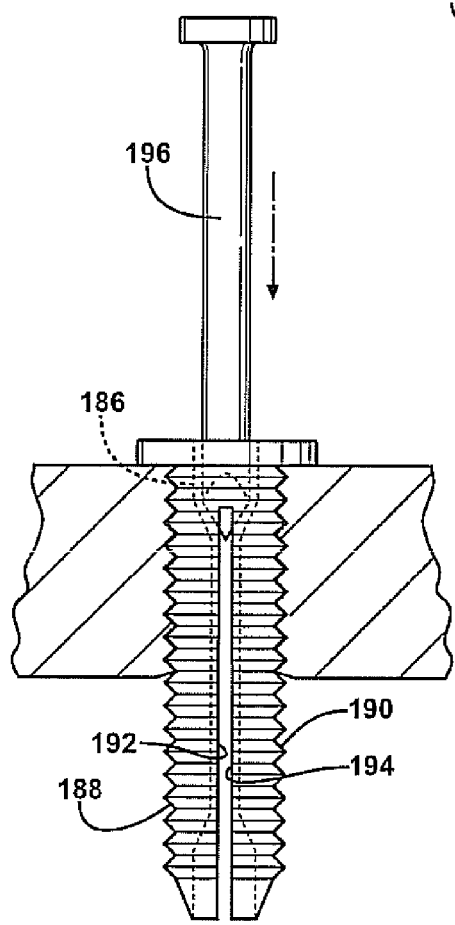
FIG. 15A is an illustration of a yet further configuration of anchoring sleeve and exhibiting first and second linearly separated and laterally displaceable halves which are actuated via an inwardly engaging spike.

FIG. 15A an illustration of a yet further configuration of anchoring sleeve 186 and exhibiting first and second linearly separated and laterally displaceable halves 188 and 190, between which is configured one or more linearly extending clearance slot (see as defined by inner opposing walls 192 and 194 established between the halves 188 and 190) and which are actuated via an inwardly engaging spike 196.

Figure 15B:
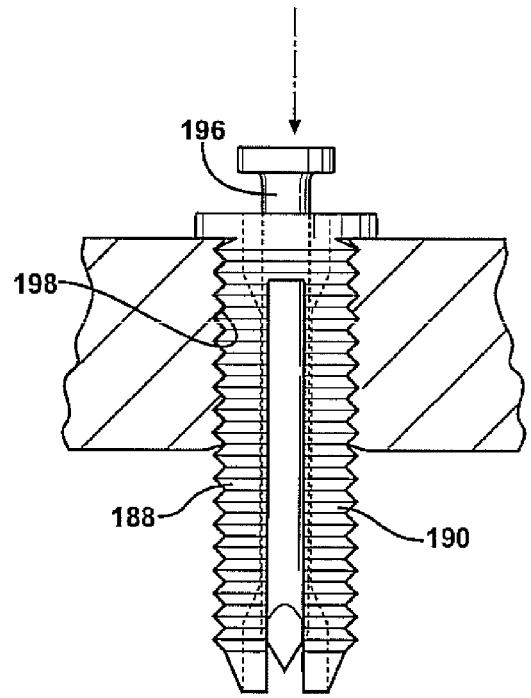
FIG. 15B is a succeeding illustration to that shown in FIG. 15A in which the first and second linearly extending and separated sleeve halves are shown in laterally displaced fashion and are biased between the inwardly displacing and engaging spike and the annular side wall associated with the bone drill holes.

Finally, and referring to FIG. 15B, a succeeding illustration to that shown in FIG. 15A is shown in which the first and second linearly extending and separated sleeve halves 188 and 190 are shown in laterally displaced fashion and inter-supported by a combination of the inwardly displacing and engaging spike 196 and the annular side wall, see at 198 associated with the bone drill hole. Again, and although not shown, it is understood that the various anchoring portions illustrated throughout the several embodiments are utilized in cooperation with an appropriately formed bone recess including a primary hole and a secondary (undercut) configured hole, and in order to provide for a permanent and secure seating environment for the (male) ball or (female) concave receiver implants as illustrated herein.

Having described my invention, other and additional preferred embodiments will become apparent to those skilled in the art to which it pertains, and without deviating from the scope of the appended claim:

I claim:

1. A shoulder implant assembly for use with a pair of joint defining bones, said implant assembly comprising:
    a spherical shaped member configured to mount in projecting fashion from a retrofitted end of a first of the joint defining bones;
    a concave shaped member configured to mount in inwardly recessed fashion from a retrofitted end of a second of the joint defining bones and which seats said spherical shaped member in a joint defining relationship established between the bones;
    a pair of mounting tabs adapted to project from a bone contacting surface of said concave shaped member and into the retrofitted end of the second joint defining bone, support pins configured for engagement at surface locations of the second bone and anchoring to said mounting tabs; and
    an anchor fastener for mounting said spherical shaped member into a concave shaped seating profile formed in the retrofitted end of the first bone, said anchor fastener further comprising a spike engaging within an elongated and deformable plasticized collar mounted to the first bone at an undercut location in communication with the further concave shaped profile, said undercut location further in alignment with an aperture formed in said spherical shaped member, a pair of semi-spherical undercut engaging portions located within said deformable collar which, upon linear translation of said spike from a direction originating through said aperture in said spherical shaped member, being contacted by said spike and caused to being laterally expanded against said plasticized collar to outwardly deform said collar within the undercut location for mounting said spherical shaped member to the first bone.

2. The assembly as described in claim 1, each of said spherical shaped member and concave shaped member being constructed of at least one of a composite hardened plastic and a softened cartilage wear surface plastic.

3. The assembly as described in claim 1, said deformable plastic collar exhibiting exterior threads.

4. The assembly as described in claim 1, said undercut portions each further comprising an inwardly tapered upper edge profile and collectively defining a pocket for receiving an inserting portion of said spike prior to outward lateral displacement.

5. The assembly as described in claim 1, at least one of said spherical and concave shape members further comprising a single layer of a composite soft plastic material having rearward extending and integrally formed portions configured so as to precisely match machined interior locations associated with the bone and in preparation for installation thereto.

* * * * *